(12) United States Patent
Linares (10) Patent No.: US 8,888,850 B2
(45) Date of Patent: Nov. 18, 2014

(54) COMBINATION SPACER INSERT AND SUPPORT FOR PROVIDING INTER-CERVICAL VERTEBRAL SUPPORT

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 548 days.

(21) Appl. No.: 12/786,088

(22) Filed: May 24, 2010

(65) Prior Publication Data

US 2010/0234958 A1    Sep. 16, 2010

Related U.S. Application Data (63) Continuation-in-part of application No. 12/273,067, filed on Nov. 18, 2008.

(60) Provisional application No. 60/988,921, filed on Nov. 19, 2007, provisional application No. 61/183,383, filed on Jun. 2, 2009.

(51) Int. Cl.
| | |
|---|---|
| *A61F 2/44* | (2006.01) |
| *A61B 17/70* | (2006.01) |
| *A61B 17/80* | (2006.01) |
| *A61F 2/30* | (2006.01) |

(52) U.S. Cl.
CPC .............. *A61B 17/70* (2013.01); *A61F 2/441* (2013.01); *A61F 2250/0018* (2013.01); *A61F 2002/30576* (2013.01); *A61F 2/44* (2013.01); *A61F 2002/3055* (2013.01); *A61F 2002/30883* (2013.01); *A61F 2002/30014* (2013.01); *A61F 2002/30378* (2013.01); *A61F 2002/30016* (2013.01); *A61B 2017/7073* (2013.01); *A61B 17/7043* (2013.01); *A61F 2220/0033* (2013.01); *A61F 2002/30904* (2013.01); *A61F 2002/30538* (2013.01); *A61F 2002/30579* (2013.01); *A61B 17/8085* (2013.01); *A61F 2250/0019* (2013.01); *A61B 17/7059* (2013.01); *A61F 2002/30471* (2013.01); *A61F 2220/0091* (2013.01); *A61B 17/7031* (2013.01); *A61F 2002/30601* (2013.01); *A61F 2250/0006* (2013.01); *A61F 2002/30578* (2013.01); *A61F 2/442* (2013.01); *A61F 2002/30841* (2013.01); *A61F 2002/30588* (2013.01)
USPC ...................................................... 623/17.12

(58) Field of Classification Search
USPC .................. 606/246–279, 99, 105; 623/17.11–17.16
See application file for complete search history.

(56) References Cited

U.S. PATENT DOCUMENTS

| | | |
|---|---|---|
| 5,522,899 A | 6/1996 | Michelson |
| 5,653,763 A | 8/1997 | Errico et al. |

(Continued)

FOREIGN PATENT DOCUMENTS

WO    2008011492 A2    1/2008

*Primary Examiner* — Mary Hoffman
*Assistant Examiner* — Michelle C Eckman
(74) *Attorney, Agent, or Firm* — Gifford, Krass, Sprinkle, Anderson & Citkowski, P.C.; Douglas J. McEvoy (57) ABSTRACT

A combination spacer insert and support for incorporating into a space defined between succeeding vertebrae. A first insert body is constructed of a composite material exhibiting at least one modulus of elasticity with a substantially cylindrical shape and is inserted within the space, such as established between a pair of previously non-consecutive vertebrae and corresponding to an absent vertebrae. An additional and exterior supported member engages locations associated with the (formerly) non-consecutive vertebrae and which, in combination with the insert body, provides a limited degree of mobility to the vertebrae.

4 Claims, 7 Drawing Sheets

(56) References Cited

U.S. PATENT DOCUMENTS

| | | | |
|---|---|---|---|
| 5,683,391 A * | 11/1997 | Boyd | 606/264 |
| 5,782,832 A | 7/1998 | Larsen et al. | |
| 6,001,130 A * | 12/1999 | Bryan et al. | 623/17.16 |
| 6,045,579 A | 4/2000 | Hochshuler et al. | |
| 6,228,085 B1 * | 5/2001 | Theken et al. | 606/289 |
| 6,447,546 B1 * | 9/2002 | Bramlet et al. | 623/17.16 |
| 6,626,904 B1 | 9/2003 | Jammet et al. | |
| 6,626,909 B2 | 9/2003 | Chin | |
| 6,641,614 B1 | 11/2003 | Wagner et al. | |
| 6,645,207 B2 | 11/2003 | Dixon et al. | |
| 6,736,850 B2 * | 5/2004 | Davis | 623/17.16 |
| 6,936,071 B1 | 8/2005 | Marnay et al. | |
| 7,201,775 B2 | 4/2007 | Gorensek et al. | |
| 7,276,082 B2 | 10/2007 | Zdeblick et al. | |
| 7,316,714 B2 | 1/2008 | Gordon et al. | |
| 7,320,707 B2 | 1/2008 | Zucherman et al. | |
| 7,344,564 B2 | 3/2008 | Sweeney | |
| 7,507,243 B2 | 3/2009 | Lambrecht et al. | |
| 7,575,577 B2 | 8/2009 | Boyd et al. | |
| 7,585,316 B2 | 9/2009 | Trieu | |
| 7,585,325 B2 | 9/2009 | Schneid et al. | |
| 7,604,654 B2 | 10/2009 | Fallin et al. | |
| 7,655,045 B2 | 2/2010 | Richelsoph | |
| 7,682,376 B2 | 3/2010 | Trieu | |
| 7,717,958 B2 * | 5/2010 | Cragg et al. | 623/17.12 |
| 7,763,052 B2 | 7/2010 | Jahng | |
| 7,766,966 B2 | 8/2010 | Richelsoph | |
| 7,776,069 B2 | 8/2010 | Taylor | |
| 8,123,808 B2 * | 2/2012 | Dewey et al. | 623/17.12 |
| 2002/0022887 A1 | 2/2002 | Huene | |
| 2002/0143329 A1 * | 10/2002 | Serhan et al. | 606/61 |
| 2002/0147497 A1 * | 10/2002 | Belef et al. | 623/17.12 |
| 2004/0015166 A1 | 1/2004 | Gorek | |
| 2004/0030398 A1 * | 2/2004 | Ferree | 623/20.32 |
| 2004/0082998 A1 * | 4/2004 | Shinomiya et al. | 623/17.11 |
| 2005/0070900 A1 * | 3/2005 | Serhan et al. | 606/61 |
| 2005/0216087 A1 | 9/2005 | Zucherman et al. | |
| 2005/0245930 A1 | 11/2005 | Timm et al. | |
| 2006/0036240 A1 | 2/2006 | Colleran et al. | |
| 2006/0084984 A1 | 4/2006 | Kim | |
| 2006/0085074 A1 | 4/2006 | Raiszadeh | |
| 2006/0241766 A1 * | 10/2006 | Felton et al. | 623/17.12 |
| 2006/0253198 A1 * | 11/2006 | Myint et al. | 623/17.12 |
| 2006/0276898 A1 | 12/2006 | Jackson | |
| 2006/0282078 A1 | 12/2006 | Labrom et al. | |
| 2007/0005062 A1 | 1/2007 | Lange et al. | |
| 2007/0083199 A1 | 4/2007 | Baccelli | |
| 2007/0093829 A1 | 4/2007 | Abdou | |
| 2007/0112428 A1 * | 5/2007 | Lancial | 623/17.12 |
| 2007/0135921 A1 * | 6/2007 | Park | 623/17.12 |
| 2007/0168036 A1 | 7/2007 | Ainsworth et al. | |
| 2007/0168039 A1 * | 7/2007 | Trieu | 623/17.15 |
| 2007/0185489 A1 | 8/2007 | Abdou | |
| 2007/0225813 A1 * | 9/2007 | Haines | 623/17.16 |
| 2007/0239278 A1 * | 10/2007 | Heinz | 623/17.15 |
| 2008/0004707 A1 * | 1/2008 | Cragg et al. | 623/17.16 |
| 2008/0021466 A1 | 1/2008 | Shadduck et al. | |
| 2008/0039943 A1 * | 2/2008 | Le Couedic | 623/17.16 |
| 2009/0112323 A1 * | 4/2009 | Hestad et al. | 623/17.12 |
| 2009/0112326 A1 * | 4/2009 | Lehuec et al. | 623/17.16 |
| 2011/0004307 A1 * | 1/2011 | Ahn et al. | 623/17.12 |
| 2011/0029084 A1 * | 2/2011 | Milbocker et al. | 623/17.16 |
| 2011/0077740 A1 * | 3/2011 | Perez-Cruet et al. | 623/17.16 |
| 2011/0224793 A1 * | 9/2011 | Fortin et al. | 623/17.12 |
| 2012/0095561 A1 * | 4/2012 | Voisard et al. | 623/17.16 |

* cited by examiner

COMBINATION SPACER INSERT AND SUPPORT FOR PROVIDING INTER-CERVICAL VERTEBRAL SUPPORT

CROSS-REFERENCE TO RELATED APPLICATIONS

This Application is a Continuation-in-part of application Ser. No. 12/273,067 filed on Nov. 18, 2008, which application claims the benefit of U.S. Provisional Application 60/988,921 filed on Nov. 19, 2007. This Application also claims the benefit of U.S. Provisional Application 61/183,383 filed on Jun. 2, 2009.

FIELD OF THE INVENTION

The present invention relates generally to inter-vertebral support braces. More specifically, the present invention discloses a combined spacer insert with or without support web for use in either or both inter-vertebral supporting and/or replacement of one ore more cervical spinal vertebrae.

BACKGROUND OF THE INVENTION

The prior art is documented with spinal column stabilizing or support implantations. A most common prior art procedure is the implanting of a titanium plate, rod or the like and which is further anchored by screws to spatially arrayed (typically non-consecutive) vertebrae for the purpose of immobilizing or fusing the spinal region, such as further to reduce pain associated with pinching of the spinal nerve column and its branches between irregularly positioned vertebrae. Conventional spinal implantations, while effective in removing or reducing nerve pain, also result, to varying degrees, in reduced dexterity of motion.

SUMMARY OF THE INVENTION

A combination spacer insert and support for incorporating into a spacing or cavity (which for purposes of this description is interpreted to include any type of enclosed space according to any dimension or configuration and which is established between inter-spinal vertebrae) defined between a spaced apart pair of vertebrae. A first insert body is constructed of a composite material exhibiting at least one modulus of elasticity with a substantially cylindrical shape and is inserted within the cavity location, such as established between a pair of previously non-consecutive vertebrae and corresponding in location to a further previously damaged or removed vertebrae. The insert body may further exhibit first and second laterally or height displaceable portions.

The insert body is further constructed of a composite plastic material including first and second plastic subset components exhibiting separate first and second modulus of elasticity. The composite plastic material may further be admixed with at least one of a metal, a ceramic and an anti-microbial material.

An additional and exterior supported member engages locations associated with the (formerly) non-consecutive vertebrae and which, in combination with the insert body, provides a limited degree of mobility to the vertebrae. The exterior supported member may further include a semi-rigid plastic with undercut engaging portions associated with first and second ends of the member. The ends can further be elastically deformable.

The insert body and exterior supported member may further be combined into a unitary component, such as further incorporating a flexible membrane supported upon a conical and apertured spine portion extending from a vertebral surface mounted end plug. Barbed anchors are provided for seating within the end plug and mounting within undercut patterns formed within the spaced apart vertebrae. A syringe is injected and a settable liquid introduced for inflating the membrane within the cavity and into supporting fashion with the vertebrae.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Referring to the succeeding illustrations, the present invention discloses a variety of combined spacer inserts, with or without support webs, straps or other interior or exterior secured members, for use in either or both inter-vertebral supporting and/or replacement of one ore more spinal vertebrae, and which includes but is not limited to cervical vertebrae as well as thoracic and lower lumbar vertebrae. As previously discussed, the present invention is further an improvement over prior art titanium plates and screws which fixedly anchor vertebrae.

Figure 1:
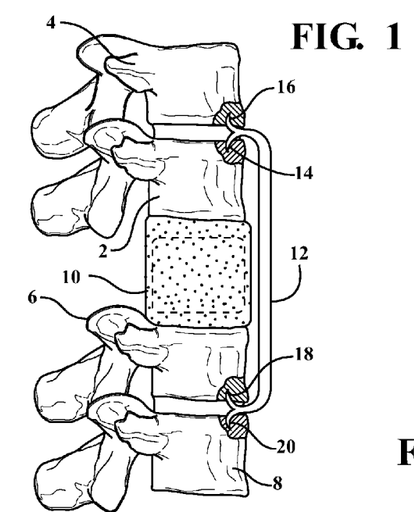
FIG. 1 is a plan illustration of a first configuration according to the present inventions and which illustrates the provision of a spacer insert installed within a space previously occupied by a removed vertebrae, in combination with an exterior secured strap or support exhibiting angled contact feet for engaging within undercut locations formed within each of first and second pairs of succeeding vertebrae located above and below the insert.

FIG. 1 is a plan illustration of a first configuration according to the present inventions and which illustrates the provision of a spacer insert 10 installed within a space previously occupied by a removed vertebrae (and which is again collectively understood to include any of a hole, cavity or the like which is generally defined as any enclosed space or configuration established between individual vertebrae). In combination, an exterior secured and generally elongated structurally supporting member 12 is provided (this further understood for purposes of each of the succeeding variants to include a generally structurally supporting strap or semi-rigid member having a desired length for interconnecting spaced apart vertebrae) and exhibits angled end located contact feet (see as further shown at 14/16 at an upper extending end and further at 18/20 for a lower extending end) for engaging within undercut defined locations formed within each of first 2/4 and second 6/8 pairs of succeeding vertebrae located at spaced distances both above and below the insert 10. Although not particularly illustrated in this view, the angled contact feet 14/16 and 18/20 engage within undercut machined recesses formed within end facing and opposing surfaces associated with each of the upper 2 & 4 and lower 6 & 8 vertebrae.

As will be further described throughout the several views presented herein, both the three dimensional and generally cylindrical shaped insert 10 and exterior elongated and structurally supporting member 12 are constructed of any of a unitary plastic, combination hard/soft plastic or composite plastic (such as further incorporating metal and/or ceramic subset admixtures). Additionally, each of the inner supported body (or insert) 10 and exterior extending and supported member 12 (as further depicted in succeeding variants described in each of FIGS. 2, 3, 4, 5, 6, 7, 9, 10, 11 and 12) include a specified bending or elastic modulus of elasticity (in the further instance of the insert 10 optionally including outer and inner varying modulii) and so as to provide desired performance and flexural properties. Such includes the desire of the assembly to provide adequate support to the spinal column to prevent pinching or damage to the spinal nerve column and branches (not shown), while providing a degree of desired flexural bending which is an improvement over prior art immobilized spinal fusion using titanium plates and screws. The use of anti-microbial additives within either of the insert and strap configurations is also contemplated.

In this fashion, and is further described in furthering detail with reference to each succeeding illustration, a non-limiting objective is again the ability to provide a desired degree of flexural support to a spinal column location in which a previously damaged vertebrae has been removed and an artificial spacer support insert has been substituted, combined with a likewise composite supporting strap or other configured elongated member being configured to securely engaging machined locations associated with successive existing vertebrae and while permitting a limited desired degree of flex or motion mimicking the natural articulation of the spinal area, and further without damaging or otherwise compromising the proximately located spinal nerve network (not shown).

Figure 2:
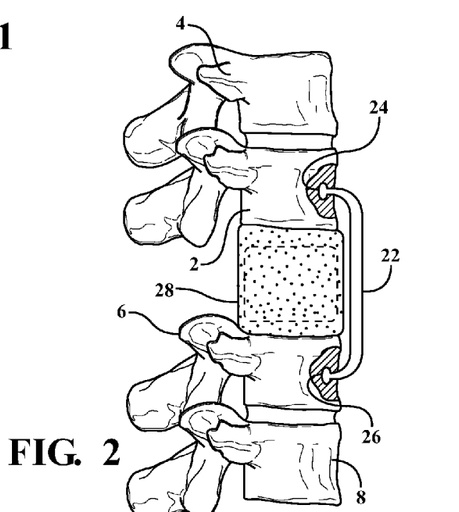
FIG. 2 is an illustration of a further configuration of exterior bracing strap exhibiting bulbous end projecting and undercut location engaging feet defined in vertebrae located on either side of an installed spacer insert.

Referring now to FIG. 2, an illustration is shown at 22 of a further configuration of exterior bracing and generally elongated structural supporting member or strap, this further exhibiting bulbous end projecting and undercut location engaging feet 24 and 26, defined in engagement with previously identified succeeding vertebrae 2 and 6 located on either side of an installed spacer insert 28. As previously described, a medical drill incorporating an appropriate configured and undercut creating drill bit (not shown) is provided for creating a desired undercut (also defined as an expanded inner recess) within exposed edge locations of each of the indicated natural vertebrae 2 and 6 (such as again in non-interfering fashion with the existing spinal nerve column and tributary network).

The construction of the insert 28 is further such that it can exhibit a combination outer softer plastic combined with a harder interior core, this intended to mimic the natural properties of existing cervical vertebrae. The bracing and supporting strap 22 can also exhibit varying hardness (or modulus of elasticity) such as further contemplating softer material incorporated into the bulbous feet 24 and 26 in order to facilitate press-fit engagement within the previously machined undercut locations associated with the adjoining vertebrae 2 and 6.

Figure 3:
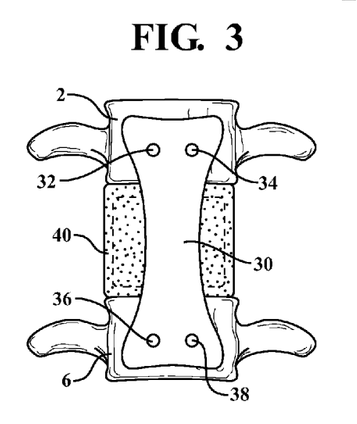
FIG. 3 is a rotated plan view of a further strap configuration and illustrating the use of multiple engaging locations for securing the strap to the adjoining vertebrae.

FIG. 3 is a rotated plan view of a further exterior member, or strap configuration 30, and illustrating the use of multiple engaging locations 32/34 and 36/38 (such as constructed in any suitable fashion including again but not limited to as shown for angled contact feet 14/16 and 18/20 for FIG. 1 and bulbous feet 24 and 26 in FIG. 2). In this fashion, the engagement locations secure the strap 30 to exposed (and again typically undercut) locations of adjoining upper and lower vertebrae 2 and 6.

An inter-disposed spacer insert 40 again exhibits such as a shortened cylinder configuration and which is positionally secured between opposing facing surfaces of the upper 2 and lower 6 vertebrae, this further defining the general boundaries of the three dimensional space to be occupied by the insert 40. As will be described in reference to succeeding variants, the insert 40 can again exhibit multi-modulus exhibiting portions (this including such as a first harder and interior plug surrounded by a second softer outer covering of specified thickness) and is further envisioned in related variants to exhibit features which facilitate adhesion or bonding of opposite end surfaces of the insert with either or both of the upper and lower situated vertebrae.

Figure 4:
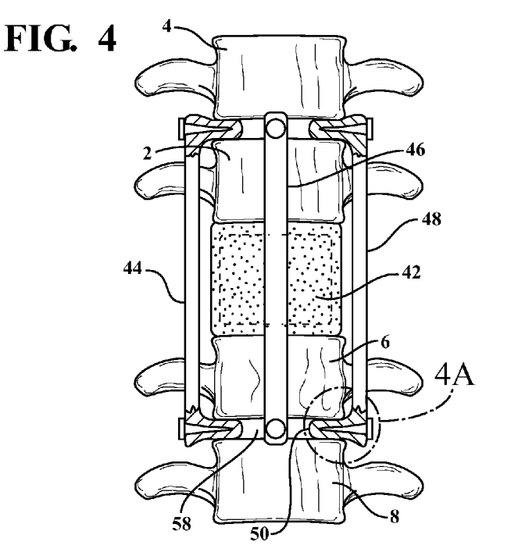
FIG. 4 illustrates a further modified strap configuration in which the spacer insert is surrounded by a plurality of individual and thin cross sectional straps arranged in a circumferential cage extending fashion.

Referring now to FIG. 4, a further modified strap configuration is shown in which a spacer insert 42 is surrounded by a plurality of individual and thin cross sectional extending structural members 44, 46, 48 arranged in a generally pseudo-circumferential or cage extending fashion. As previously described, the insert 42 can (but are not required to) exhibit properties which promote artificial fusion to the adjoining vertebrae 2 and 6 (such as will be further described including the roughening of the insert spacer end surfaces to promote bone marrow growth and adhesion with the adjoining vertebrae).

Figure 4A:
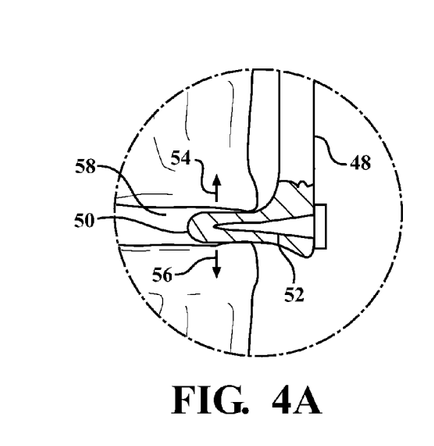
FIG. 4A is an enlarged partial view of an end-engaging location associated with a selected strap in FIG. 4 and further showing a deformable end-located pocket which, upon engagement of an insertable fastener such as a screw or nail is outwardly expanded to seat within a recess defined within inwardly and opposing extending surfaces of adjoining vertebrae.

FIG. 4A is an enlarged partial view of an end-engaging location 50 also shown in FIG. 4 associated with selected exterior structural member 48 and further showing a deformable end-located pocket which, upon engagement of an insertable fastener 52 such as a screw or nail in inserting fashion through an exterior location and within the location 50, outwardly expands the end pocket (see directional arrows 54/56) to seat within recess 58 (also again shown in FIG. 4) defined within inwardly and opposing extending surfaces of the lower adjoining vertebrae 6 and 8. In this fashion, the use of machined undercut portions can be substantially reduced or eliminated, with the required retaining forces being provided by the expanded holding forces associated with the elastically deformable/expandable end feet (e.g. at 48).

Figure 5:
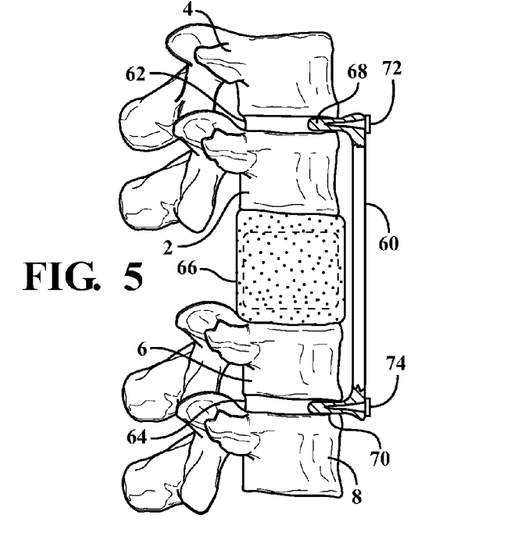
FIG. 5 is an illustration of a related spacer and strap configuration and illustrating a modified fastener engagement configuration for securing the strap at first and second vertebrae boundary locations.

FIG. 5 is an illustration of a related spacer and strap configuration and illustrating a modified fastener engagement configuration, at 60, for securing at first and second vertebrae boundary locations 62 and 64 corresponding to the spaced defined between the upper pair 2/4 of vertebrae and lower pair 6/8 arranged on opposite sides of a suitable artificial spacer insert 66. The strap 60 is again semi-rigid in construction and exhibits a desired modulus of flexibility with similarly configured engaging end fee 68 and 70 respectively receiving insertable fasteners 72 and 74 for outwardly expanding the same (in similar fashion to that previously shown in FIG. 4A) in engaging fashion within the interspatial boundary locations 62 and 64.

Figure 6:
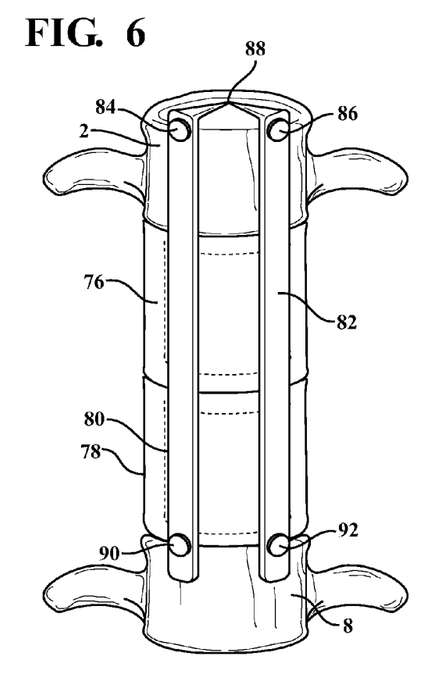
FIG. 6 is a perspective illustration of another variant in which a pair of spacer inserts are provided along with a further configuration of exterior mounting supports for engaging upper and lower adjoining vertebrae.

FIG. 6 is a perspective illustration of another variant in which a pair of further configured spacer inserts 76 and 78 are provided in successive adjoining fashion for substituting for a pair of missing vertebrae (these including the previously identified space filled by spacer insert 76 and an additional space corresponding to removed lower vertebrae 6 and its substitution by second spacer insert 78). A corresponding configuration of exterior mounting supports includes additionally illustrated and alternately configured elongate members 80 and 82 for engaging upper 2 and lower 8 adjoining vertebrae at the locations indicated.

As further illustrated, the upper engaging location includes vertebral undercut edge engaging fasteners 84 and 86 (with further end extending portions of the exterior members 80 and 82 optionally meeting at a common terminating location 88). The lower engaging location of the members 80 and 82 can further exhibit additional engaging feet 90 and 92 for engaging the interstitial boundary 64 (see also FIG. 5) existing between spacer insert 78 (or previously removed lower disk 6) and succeeding lower disk 8.

Figure 7:
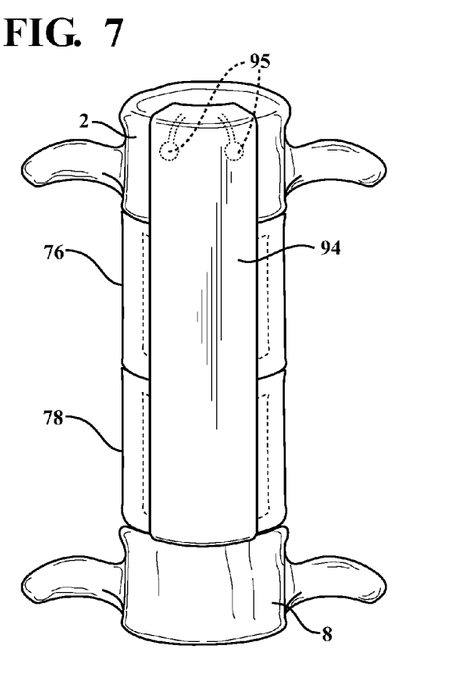
FIG. 7 is another illustration of a dual spacer insert arrangement in combination with a widened and exterior supporting strap.

FIG. 7 is another illustration of a dual spacer insert arrangement, again shown at 76 and 78, this in combination with a widened and exterior supporting strap or member as further shown at 94 and which exhibits a unitary, relatively thin and widened configuration for supporting the pair of insert spacers 76/78 between upper 2 and lower 8 existing vertebrae. As previously described, associated end engaging feet, see as depicted in phantom at 95 curling inwardly from selected upper angled end of the strap 94, can also include inwardly angled and undercut (or outwardly elastically deformable) portions for securely mounting the strap 94 at upper and lower locations to the existing vertebrae.

Figures 8A, 8B:
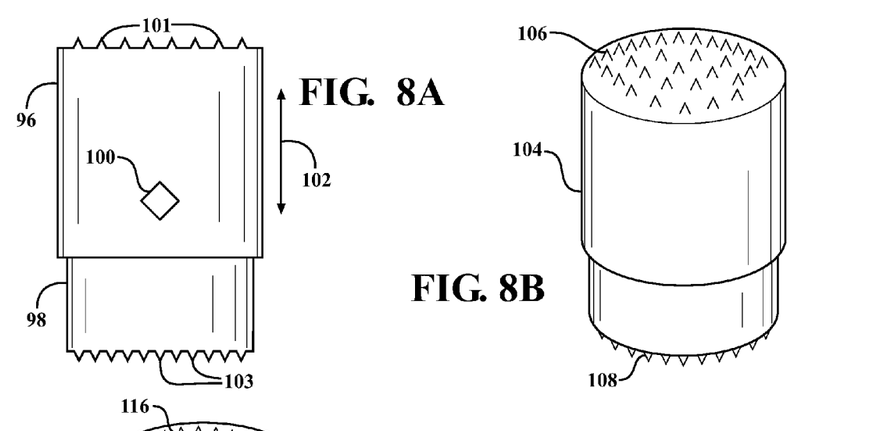
FIG. 8A is an illustration of a key engageable and outwardly expandable insert according to a further variant.
FIG. 8B is an alternately configured insert to that shown in FIG. 8A and again exhibiting end surface undercut patterns for promoting bone adhesion and growth when installed between succeeding vertebrae.

FIGS. 8A-8D illustrate a collection of alternately configured spacer inserts and such as which complement those previously shown and described. Referring first to FIG. 8A, an illustration is shown of a key engageable and outwardly expandable insert according to a further variant and including upper 96 and lower 98 interconnected and respectively displaceable halves. Key insert location 100 is further shown and, upon being engaged by a suitable surgeons key (not shown) incorporates a suitable mechanism interconnecting with bevel gears or the like and which, upon being rotated, exerts a bias against and actuates the halves 96 and 98 to laterally expand in the multi-directional fashion referenced by arrow 102. Individual surface undercut or roughened recess patterns are depicted at 101 and 103 on opposite end engaging surfaces of the displaceable halves 96 and 98.

Figure 8C:
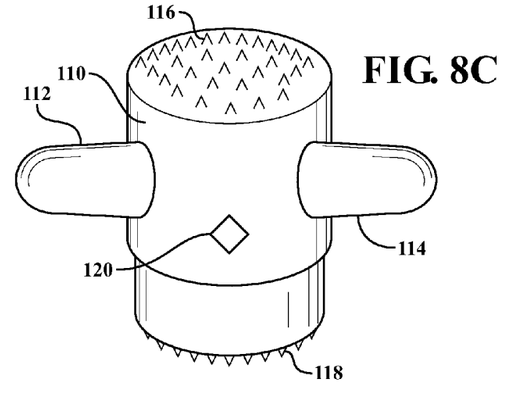
FIG. 8C is an illustration of another configuration of a key accessible and expandable insert exhibiting laterally expandable wing portions in combination with fusion/growth promoting end surface undercut patterns.

FIG. 8B is an alternately configured insert 104 to that shown in FIG. 8A and again exhibiting end surface undercut or roughened recess patterns, see further at 106 and 108, for promoting bone adhesion and growth when installed between succeeding vertebrae. FIG. 8C is an illustration of another configuration of a key accessible and expandable insert 110 exhibiting laterally expandable wing portions, at 112 and 114, these provided in combination with fusion/growth promoting end surface undercut patterns (see upper pattern 116 and lower pattern 118). A key access location is provided at 120 (similar to that identified at 98 in FIG. 8A) and communicates a separate key with an internal mechanism which, upon actuating, influences the wing portions 112 and 114 to laterally outwardly displace in contacting fashion with appropriately configured edge wall locations associated with adjoining vertebrae.

Figure 8D:
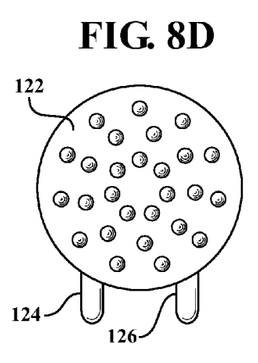
FIG. 8D is a top view of an insert according to another variant.
Figure 8E:
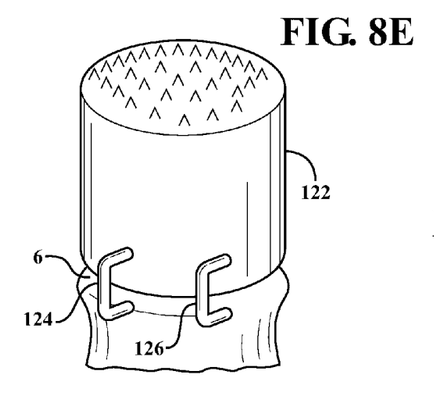
FIG. 8E is perspective view of the insert shown in FIG. 8D and illustrating the feature of edge extending and engaging tabs for mounting the spacer to an existing and succeeding vertebrae.

Referring further to FIG. 8D, a top plan view is shown of a generally disc shaped spacer insert 122 according to another variant. FIG. 8E is a perspective view of a most bottom cutaway slice or portion of the insert 122, such as shown in FIG. 8D, and additionally illustrating edge extending and inwardly angled/engaging tabs 124 and 126 for mounting the spacer to an existing and succeeding vertebrae 6. As previously described, undercut engaging recesses can be defined in the edge extending sides of the succeeding vertebrae 6 and in order that the insert 122 be securely mounted in place, such as prior to natural bone adhesion/growth which subsequently fixes the insert in position.

Figure 9:
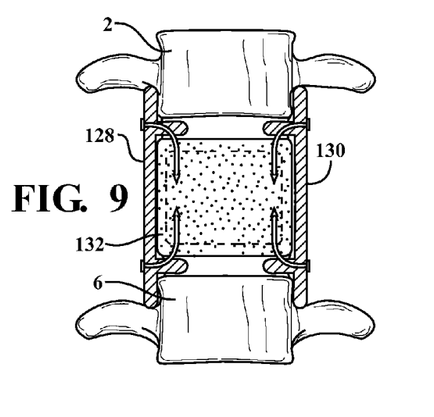
FIG. 9 is a plan view illustration of a pair of exterior mounting members in combination with an insert spacer according to a yet further embodiment.
Figure 9A:
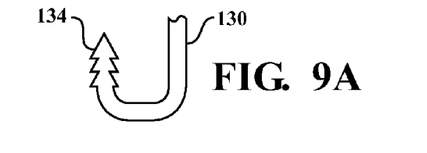
FIG. 9A is an enlarged partial illustration showing a configuration of a selected undercut engaging portion associated with an exterior mounting member.

FIG. 9 is a plan view illustration in cutaway of a pair of exterior mounting members 128 and 130, these in combination with an insert spacer 140 according to a yet further embodiment. As further shown in FIG. 9A, an enlarged partial illustration depicts one configuration of a selected mounting member 130 which further exhibits a selected undercut engaging portion 134. The engaging portion 134 exhibits an end most pseudo-serrated arrow configuration which is contributes additional restraining force when press fit into a recess previously machined in undercut fashion within the opposing end faces of the upper 2 and lower 6 vertebrae positioned relative to the spacer insert 132.

Figure 9B:
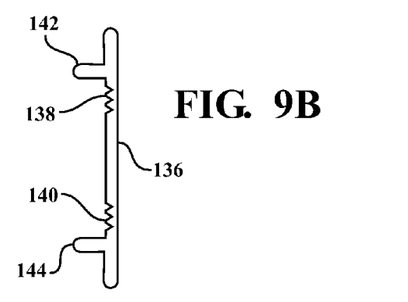
FIG. 9B is an illustration of a mounting member exhibiting flexural joint locations proximate end disposed and intervertebral space engaging portions associated with the mounting member.

As further shown in FIG. 9B, the mounting member illustrated at 136 incorporates flexural joint locations 138 and 140 proximate end disposed and inter-vertebral space engaging portions 142 and 144 associated with the mounting member. The flexural joint locations 138/140 further include such as "V" shaped or otherwise configured notches (or weakening portions) which are designed into the member 136 and which function to provide a degree of additional and desired flexural bending proximate the engaging portions 142 and 144, such as further along the mounting interfaces with the adjoining vertebrae.

Figure 10:
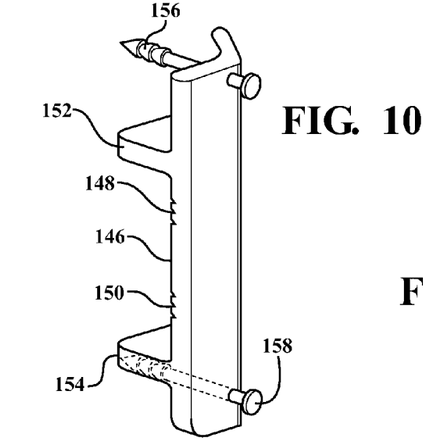
FIG. 10 is an illustration of another elongate mounting member also including the features of flexural promoting joints defined within the member at locations proximate intervertebral space engaging portions, in combination with screws extending through end locations of the member.

Referring now to FIG. 10, an illustration is shown of another elongate mounting member 146, this also including the features of the flexural promoting joints (or notched recesses) 148 and 150 defined within the member 146 at locations proximate inter-vertebral space engaging portions 152 and 154. The engaging portions 152 and 154 as shown exhibit an additional degree of depth for inserting in supporting and shouldering fashion within and interstitial spaces defined between the spacer insert and adjoining vertebrae and, in further combination with screws 156 and 158 extending through proximate end locations of the member 146, engage previously machined apertures (or undercut patterns) associated with mating locations of the adjoining vertebrae. In use, the plastic joint exhibits desired flexural aspects which accommodate compressive forces exerted by the adjoining vertebrae, it further being understood that a degree of vertebral bone exerted pressure is desired in order to promote subsequent fusion of the strap to the spinal vertebrae.

Figure 11:
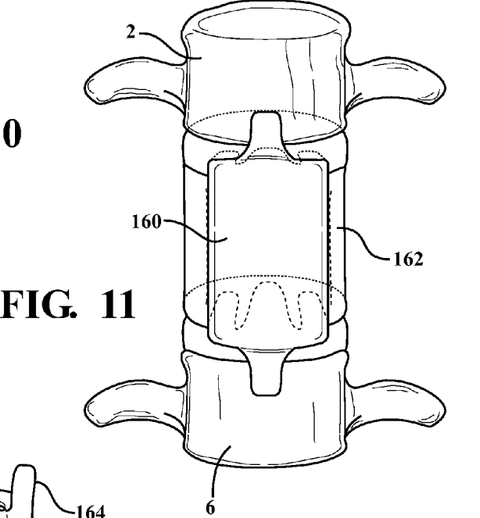
FIG. 11 is an illustration of another design of flexural supporting strap extending between spaced apart vertebrae and across a substitute insert spacer according to a further embodiment.
Figure 12:
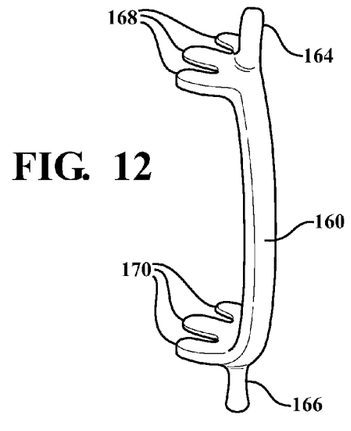
FIG. 12 is a rotated illustration of the supporting strap shown in FIG. 11 and illustrating both lineal end extending portions as well as inwardly extending and inter vertebral engaging portions.

FIG. 11 is an illustration of another design of flexural supporting strap 160 extending between spaced apart vertebrae 2 and 6, and across a substitute insert spacer 162 according to a further embodiment. FIG. 12 is a rotated illustration of the supporting strap 160 shown in FIG. 11 and better illustrating both lineal end extending portions 164/166 incorporated in combination with inwardly extending and inter vertebral engaging portions 168/170. As collectively illustrated, this strap design promotes a more rigid supporting environment around the spacer insert 160 and can again utilize such as undercut engaging patterns and/or end extending and elastically deformable portions.

Figure 13:
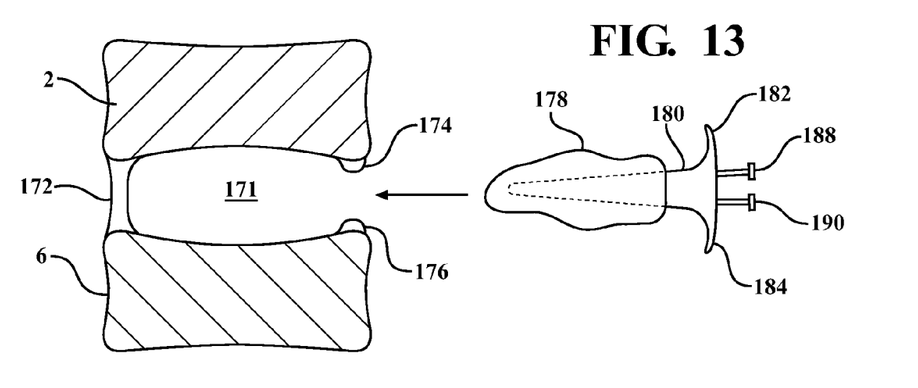
FIG. 13 is a side plan view in exploded fashion and illustrating an artificial disc replacement mechanism according to a still further preferred embodiment exhibiting a hollowed out area corresponding to a previously prepared location including rear disc located support and front undercut defined support locations, and within which is installed a balloon jack with forward sealing plug.

Referring now to FIGS. 13-17, a series of illustrations are shown of an artificial disc replacement mechanism according to a yet further preferred embodiment. The disc replacement mechanism can be incorporated in substitution or combination with the generally cylindrical shaped insert supports (such as at 10) and, although not shown in FIGS. 13-17, can be further utilized with any version of exterior supporting and engaging member as previously illustrated and described. FIG. 13 is a cutaway side plan view in exploded fashion and illustrating a hollowed out area, generally at 171 corresponding to a previously prepared location between existing upper vertebrae 2 and lower vertebrae 6, and including a rear disc located support or column 172 and front undercut pattern defining support locations 174 and 176 (these exhibiting front located and inwardly opposing protuberances).

Figure 17:
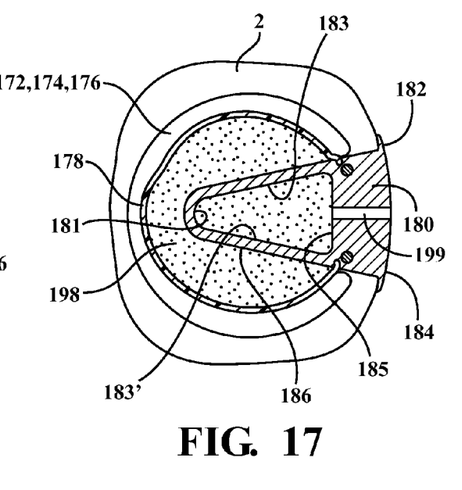
FIG. 17 is a top view cutaway illustration taken along line 17-17 of FIG. 16 and further illustrating the operational configuration of the disc replacement mechanism.

As is further evident from reference to subsequent illustration FIG. 17, the rear column 172 in combination with the front support location 174/176 can be incorporated into a single unitary component which is interconnected in three dimension and, as further shown in common referenced fashion in the height-wise cutaway of FIG. 17, collectively defines a general three dimensional interior cavity for seating an inflatable membrane (or balloon) 178. Also shown is a forward sealing plug 180 engageable with the flexural/inflatable membrane. The plug 180 in turn includes an exterior configuration with flange extending edges 182 and 184 (see both FIG. 17 and FIG. 14A) which, upon installation within the cleaned out area, extends over the exterior edges of the existing vertebrae 2 and 6 in the manner illustrated.

Figure 14:
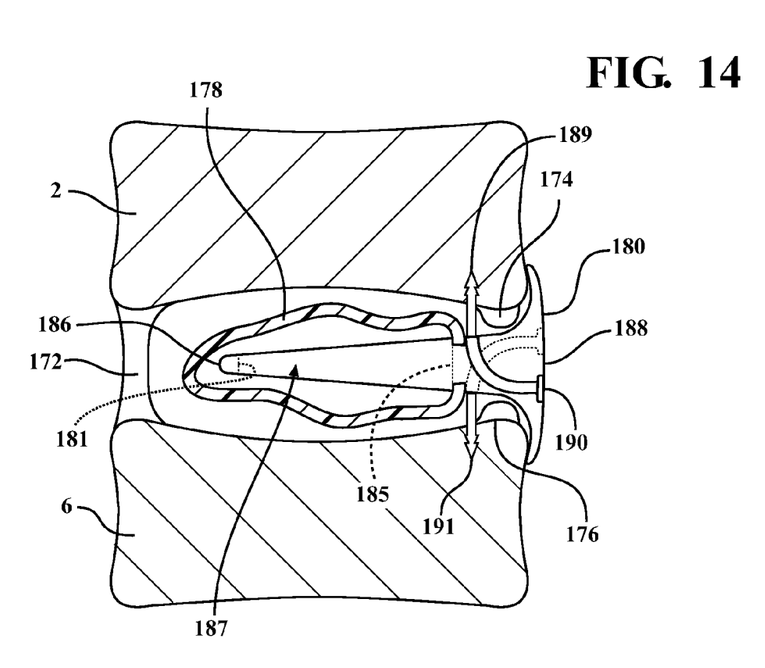
FIG. 14 is a succeeding an intermediate assembled illustration showing the balloon jack inserted within the prepared disc area, such that an apertured and conical shaped spine supports an inside of the bladder within the apertured area, and at which angled barb anchors associated with the outer plug are displaced into aligning undercuts defined in upper and lower opposing locations associated with upper/lower succeeding vertebrae.

FIG. 14 is a succeeding and intermediate assembled illustration to that shown in FIG. 13 and illustrating the outer membrane with inner actuating balloon jack 178 in an initially inserted generally flaccid condition within the prepared disc area, further such that an elongated spine portion 186 of the plug 180, upon installation, is configured so as to support an inside of the bladder 178 during press fit insertion within the apertured area. At this point, angled barb anchors 188 and 190 associated with the outer plug 180 are displaced through mating and angled apertures (likewise enumerated in FIG. 14B) defined in depth extending fashion within the plug 180, and so that such as serrated edge portions 189 and 191 of the anchors 188 and 190 seat into aligning undercuts (see further at 192 and 194 in FIG. 14A) defined in upper and lower opposing locations associated with the upper/lower succeeding vertebrae 2 and 6, and in order to press-fit the barbed anchors into the adjoining vertebral bone locations.

Figure 14A:
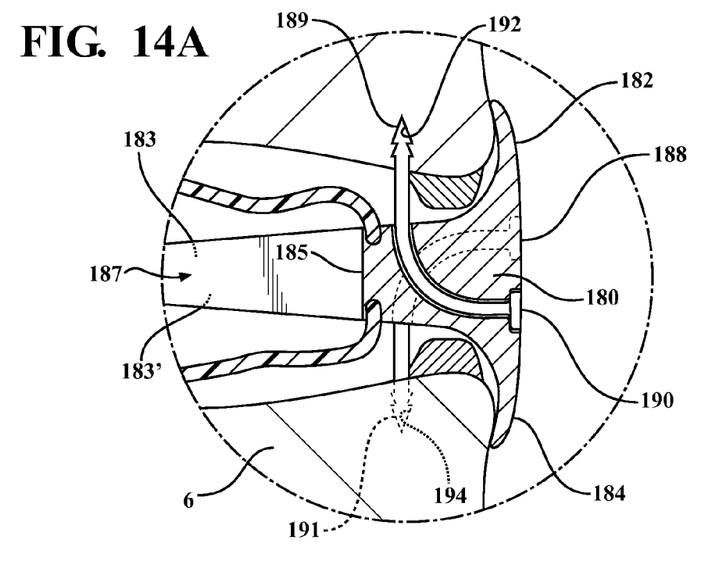
FIG. 14A is an enlarged inset view taken from FIG. 14 and better illustrating the engagement of the angled barb anchors projecting from the plug with the aligning undercuts formed in the spatially opposing vertebrae.
Figure 14B:
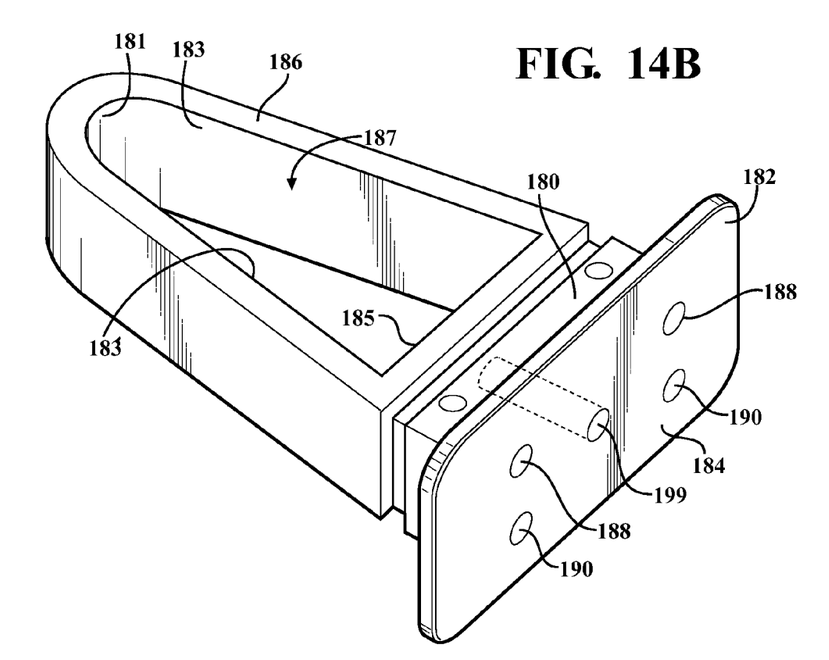
FIG. 14B is a perspective view of the insertable jack illustrated in each of FIGS. 14 and 14A and again showing the end plug and conical spine shaped support.

FIG. 14A is an enlarged inset view taken from FIG. 14 and better illustrating the engagement of the angled barb anchors 188 and 190 projecting from the plug 180, with the aligning undercuts 192 and 194 formed in the spatially opposing vertebrae. As is further best shown in FIG. 14B, the spine portion 186 establishes a generally open interior 187 (accessible from inlet location 199 of the plug 180) established by a series of interconnecting inner edges including distal proximate edge 181, spaced apart and lengthwise extending edges 183 and 183' and interconnecting proximal edge 185, the purpose for which being to provide an inner spine support for charging a polymeric settable material through the spine 186 so as to flow within the flexible and expansible membrane 178 within which the spine 186 is internally supported.

Figure 15:
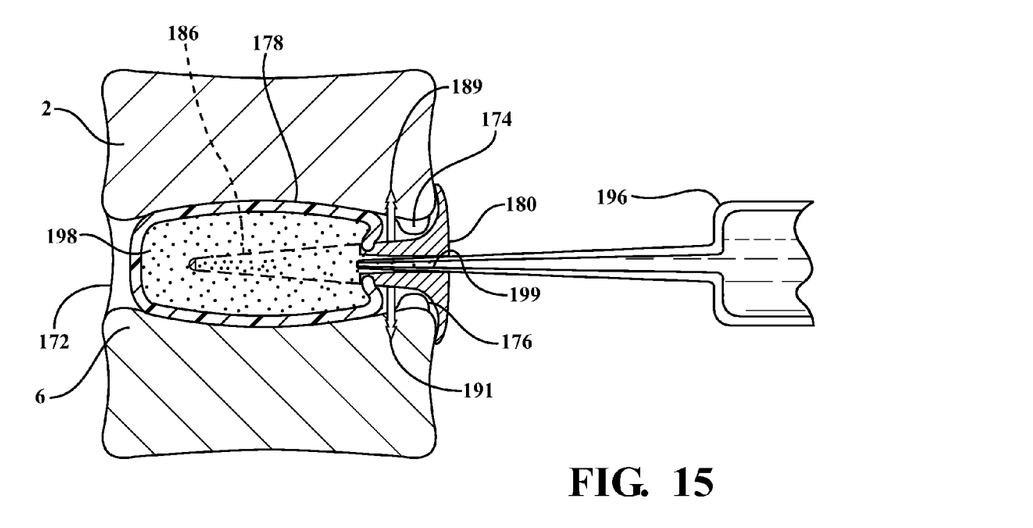
FIG. 15 is a further succeeding illustration in which a syringe charged with a settable fluidic material is injected through the plug, through the apertures associated with the conical spine and in order to expand the bladder to abut the front and rear locations of the vertebral defined space and to bias against the upper and lower adjoining vertebrae.

Referring now to FIG. 15, a further succeeding illustration is shown in which a syringe like component 196 is charged with the settable fluidic material 198 (such as including a two part fast reacting polymer or the like) is injected through a central injection aperture 199 defined in the plug 180, through the interior 187 associated with the inner extending spine 186, and in order to expand the bladder/membrane 178 in the manner illustrated so as to abut the front (174/176) and rear (172) locations of the vertebral defined space, and to bias against the upper 2 and lower 6 adjoining vertebrae.

Figure 16:
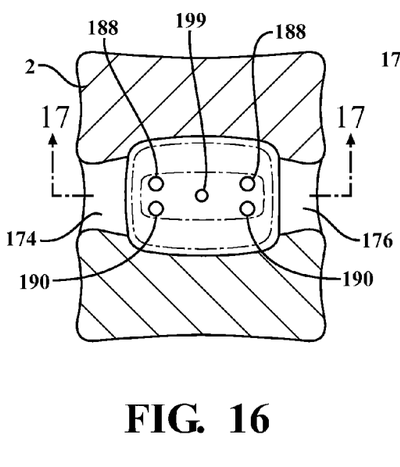
FIG. 16 is a rotated front view of the disc replacement mechanism and illustrating first and second pairs of angularly displaceable/engageable anchors combined with a central injection aperture.

FIG. 16 is a rotated front view of the disc replacement mechanism and illustrating one non-limiting arrangement of first 188 and second 190 pairs of angularly displaceable/engageable anchors, combined with the central injection aperture 199 for receiving an inserting tip of the syringe 196. Finally, FIG. 17 again illustrates a top view cutaway illustration taken along line 17-17 of FIG. 16 and further illustrating the operational configuration of the disc replacement mechanism.

The artificial spinal disc replacement system disclosed in FIGS. 13-17 possesses multiple advantages in both design and materials relative to existing systems. In contrast to the most commonly used designs, these using metal end-plates provided in direct contact with the bodies of the adjoining vertebrae that lie both superior (above) and inferior (below) to the inter-disposed replacement disc, the present invention places a plastic/metal or plastic/ceramic composite alloy material exhibiting a modulus of elasticity very similar to human cartilage in direct contact with these vertebral surface. This much more closely simulates the situation existing in a real human spine, and avoids the unwanted consequences of bone re-sorption which can otherwise occur when a hard metal is placed in direct contact with a relatively softer bone. A further advantage over existing systems is that the present design does not require any shaving or reshaping of the vertebral bodies above and below the disc prosthesis, the rendering multi-level disc replacement a feasible option.

The procedure for installing the artificial disc system requires an anterior surgical approach similar to what is used currently for anterior discectomy and fusion procedures. The native (natural) disc material is removed through an incision in the anterior longitudinal ligament, and part of the posterior longitudinal ligament is removed in conjunction with the discectomy (also termed discotomy and relating to the excavation or removal of an inter-vertebral disc), with the lateral columns left intact. The balloon is placed into the now empty disc space and saline is injected until optimum vertebral spacing is obtained. The saline is then withdrawn and the volume noted and becomes the reference volume at which the balloon is removed.

At this point, another balloon incorporated into the system is introduced into the disc space and a liquid plastic alloy is injected into the balloon up to a volume slightly less than the reference volume of the saline. Finally, the outer balloon is injected with a small volume another liquid plastic alloy, bringing the total volume of plastic injected up to the reference volume. The two liquid plastic alloys chemically react and fuse/harden into the final form.

The resulting artificial disc exhibits a thin shell of a plastic with a modulus of elasticity very similar to human cartilage, with the inner portion of the disc exhibiting a somewhat more viscous modulus, such as further similar to native vertebral nucleus pulposus. The great advantage of this system over existing systems is that it achieves an even distribution of normal stresses and control of stresses in all planes.

In use, the artificial disc system functionally operates as a real disc which is held firmly in place and presented from anterior migration using a low-profile plastic clip system that is firmly anchored in cortical bone of the vertebral body above and below the replacement disc. Anti-microbial substances are integrated into the composite matrix associated with plug, balloon and settable/curable liquid and prevent bacterial contamination of the device. The replacement disc also provides a lower cost item than conventional discectomy/discotomy procedures and fusion, preserves spinal motion, and generally renders prior art fusion techniques obsolete.

Having described my invention, other and additional preferred embodiments will become apparent to those skilled in the art to which it pertains, and without deviating from the scope of the appended claims.

I claim:

1. An artificial disc replacement mechanism adapted for being installed within a reconditioned interior space established between successive vertebrae, said mechanism comprising:
   a rigid elongated body exhibiting a generally open conical shape and having a pair of spaced apart and lengthwise edges extending from a proximal edge and joining at a distal tapered edge, a sealing plug extending from said proximal edge and having outwardly extending lip edges which are adapted to overlay exterior surfaces of the successive vertebrae, an injection aperture communicating an exterior face of said plug with an open interior bounded by said rigid body;
   an inflatable membrane having an open end secured about a perimeter extending edge of said rigid body at a location proximate said sealing plug, said membrane extending over and enclosing said rigid elongated and open body in an initially flaccid and deformable condition;
   anchors displacing through apertures defined within said end plug and adapted to being engaged within each of the successive vertebrae so that said rigid body and supported membrane are suspended in inwardly extending and non-contacting fashion relative to opposing interior vertebral surfaces and within the reconditioned interior space; and
   a volume of a settable fluidic material introduced through said injection aperture and, upon passing through an interior of said sealing plug and flowing outwardly around said rigid body and against an interior of said membrane, progressively filling and causing outward expansion of said inflatable membrane away from said rigid body and to a supporting condition in contact with inner and opposing surfaces of the vertebrae defining the reconditioned interior space.

2. The disc replacement mechanism as described in claim 1, further comprising a separate member engaging locations with the succeeding vertebrae and which, in combination with said flexible membrane, establishing a limited degree of mobility to the vertebrae.

3. The disc replacement mechanism as described in claim 1, further comprising at least one syringe with a tip insertable within said injection aperture for introducing said settable fluid as a two part fast reacting polymer.

4. The disc replacement mechanism as described in claim 1, said anchors further comprising first and second pairs of arcuate shaped and barbed anchors displacing through mating and angled apertures defined in depth extending fashion through said plug which align with undercut patterns adapted to being formed in the vertebrae and in the form of proximal located and inwardly opposing protuberances extending into the reconditioned interior space.

\* \* \* \* \*